United States Patent [19]

Vishwakarma et al.

[11] Patent Number: 5,675,015

[45] Date of Patent: Oct. 7, 1997

[54] PROCESS FOR THE PREPARATION OF BENZOTRIAZOLE DERIVATIVES

[75] Inventors: Lal Chand Vishwakarma, Rochester; Victor LaVonne Mylroie; Louis Francis Valente, both of Fairport; Barry Francis Briffa, Leicester, all of N.Y.

[73] Assignee: Eastman Kodak Company, Rochester, N.Y.

[21] Appl. No.: 611,964

[22] Filed: Mar. 7, 1996

[51] Int. Cl.⁶ .................................................. C07D 249/20
[52] U.S. Cl. ........................................ 548/260; 548/259
[58] Field of Search ................................ 548/259, 260

[56] References Cited

U.S. PATENT DOCUMENTS

| | | | |
|---|---|---|---|
| 3,978,074 | 8/1976 | Jancis | 260/308 |
| 4,089,839 | 5/1978 | Jancis | 260/45.8 |
| 4,230,867 | 10/1980 | Kintopf et al. | 548/260 |
| 4,363,914 | 12/1982 | Long et al. | 548/257 |
| 4,642,350 | 2/1987 | Davatz et al. | 548/260 |
| 4,973,702 | 11/1990 | Rody et al. | 548/261 |
| 4,999,433 | 3/1991 | Prestel et al. | 548/260 |
| 5,032,498 | 7/1991 | Rody et al. | 430/512 |
| 5,104,992 | 4/1992 | Fukuoka et al. | 548/260 |
| 5,187,289 | 2/1993 | Fukuoka et al. | 548/260 |
| 5,276,161 | 1/1994 | Prestel et al. | 548/260 |

*Primary Examiner*—Patricia L. Morris
*Attorney, Agent, or Firm*—Edith A. Rice

[57] ABSTRACT

2-(2'-Hydroxyphenyl)-2H-benzotriazoles of formula (I):

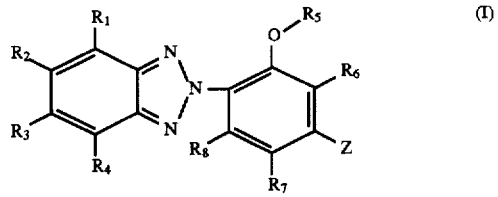

wherein:

$R_1$, $R_2$, $R_3$, $R_4$, $R_5$, $R_6$, $R_7$, $R_8$ and Z are defined in the specification, are prepared by catalytic hydrogenation of a suitable o-nitroazo dye compound in the presence of a PtS, Pt, Pd, Pt/Pd or other noble metal hydrogenation catalyst, in the presence of a base, an acid and a hydroxylic solvent.

24 Claims, No Drawings

PROCESS FOR THE PREPARATION OF BENZOTRIAZOLE DERIVATIVES

FIELD OF THE INVENTION

The present invention relates to a process for synthesizing 2-(2'-hydroxyphenyl)benzotriazole derivatives which are useful ultraviolet absorbing compounds as such or as precursors for them.

BACKGROUND OF THE INVENTION 2-(2'-Hydroxyphenyl)benzotriazole compounds are known in the art as valuable UV absorbers. They are widely used in practice as light stabilizers for a large number of substrates, for example stabilizing thermoplastics and coating materials (for example varnishes), but also in various recording materials (for example in photographic layers and papers and in printing inks and printing papers) and in textiles. Such compounds are particularly useful in silver halide photographic elements particularly for protection of yellow, magenta and cyan image dyes from fading in color photographic prints.

In accordance with the importance of these compounds, an extremely large number of processes for their preparation has been reported. The majority of them start from the corresponding o-nitrophenyl azo dye compounds and utilize reductive cyclization by various reduction methods. One of these reduction methods is catalytic hydrogenation, which has been described in a number of publications (for example, see U.S. Pat. Nos. 3,978,074, 4,089,839, 4,230,867, 4,363,914, 4,642,350, 4,999,433, 5,104,992, 5,187,289 and 5,276,161.)

The basic reaction can be represented by the following equation.

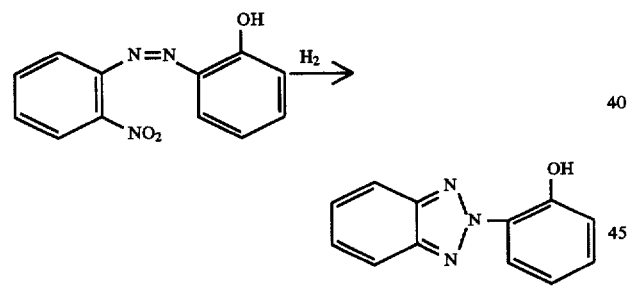

The benzo ring of the benzotriazole group and the hydroxyphenyl group can be substituted with one or more substituents. However, the prior art methods result in low yields, can be used only if the benzo and hydroxyl phenyl rings are substituted with certain substituents, result in undesired dehalogenation when the benzo ring is substituted with a halogen atom, and/or result in undesired N-oxide formation. It would be desirable to have a process for the catalytic hydrogenation of o-nitrophenyl azo dye compounds to the corresponding benzotriazole compounds that overcomes the disadvantages of the prior art processes.

SUMMARY OF THE INVENTION

We have now discovered that if an acid is added to the reaction mixture, the catalytic hydrogenation process of the prior art for converting a o-nitrophenyl azo dye compound to the corresponding benzotriazole compound is greatly improved.

One aspect of this invention comprises a process for the preparation of 2-(2'-hydroxyphenyl)-2H-benzotriazole derivatives of the formula (I):

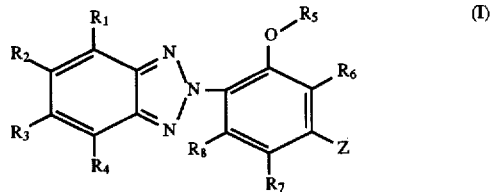

wherein $R_1$, $R_2$, $R_3$, $R_4$, $R_5$, $R_6$, $R_7$, are independently: H; halogen; $NH_2$; cyano; —$(CH_2)_pCO_2Y$ where Y is H or a 1 to 12 carbon atom alkyl or 6 to 20 carbon atom aryl and p is 0 to 20; 1 to 12 carbon atom carbamoyl group; 0 to 18 carbon atom sulfido group; 0 to 12 carbon atom sulfonyl group; 0 to 12 carbon atom sulfonato group; 0 to 12 carbon atom sulfonamido group; 1 to 18 carbon atom alkyl group; 1 to 18 carbon atom alkoxy group; 6 to 20 carbon atom aryl group; 5 to 20 atom heteroaryl group having 1 to 4 hetero atoms selected from O, N, S, P or Si; 6 to 20 carbon atom aryloxy group; or any two or more of adjacent ones of $R_1$ through $R_4$ may form, together with the carbon atoms of the benzene ring to which they are attached, a 1 to 10 carbon atom alicyclic group, a 6 to 20 carbon atom aromatic group or a 5 to 20 atom heteroaryl group having 1 to 4 heteroatoms selected from O, N, S, P or Si;

$R_5$ is H, acetyl, p-toluenesulfonyl or dialkylcarbamyl;

$R_8$ is H or OX where X is H or a 1 to 6 carbon alkyl, acetyl, benzyl, benzoyl, p-toulenesulfonyl or dialkylcarbamyl group;

Z is H, OH, a 1 to 6 carbon atom alkyl, 1 to 6 carbon atom alkoxy, 2 to 10 carbon atom acyloxy, 6 to 12 carbon atom arylsulfonyloxy or 2 to 12 carbon atom dialkylcarbamato group or a group of the formula:

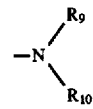

wherein each of $R_9$ and $R_{10}$ is independently H, 1 to 6 carbon atom alkyl group, 1 to 12 carbon atom acyl group, 6 to 20 carbon atom alkylsulfonyl group, arylsulfonyl group, heteroarylsulfonyl group, or 2 to 12 carbon atom dislkylcarbamato group, said process comprising the catalytic hydrogenation of an azo dye compound of formula (II)

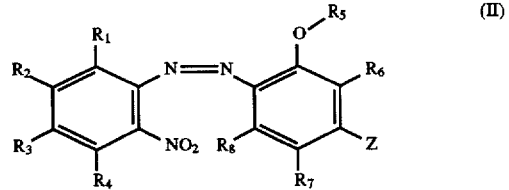

wherein $R_5$–$R_8$ and Z are as defined above for formula I, and $R_1$–$R_4$ are as defined above or a $NO_2$ group, in the presence of a noble metal hydrogenation catalyst, a base and an acid in a reaction medium comprising a polar hydroxylic solvent and, optionally, a non-hydroxylic solvent.

ADVANTAGEOUS EFFECT OF THE INVENTION

The process of this invention can be used to hydrogenate o-nitrophenyl azo dye compounds that can be substituted with a wide variety of substituents. Further, the process provides high yields of the desired benzotriazole compound without significant formation of undesired N-oxide compound. In the event the o-nitrophenyl azo dye compounds is substituted with a halogen atom, selection of an appropriate acid can either allow or inhibit dehalogenation of the benzo or hydroxy phenyl ring, as desired.

DETAILED DESCRIPTION OF THE INVENTION

The starting compounds of the formula (II) are known, for example from the references cited above or from U.S. Pat. Nos. 4,973,702 and 5,032,498, the disclosures of which are incorporated herein by reference. They can be prepared, for example, by diazotization of an o-nitroaniline of the formula:

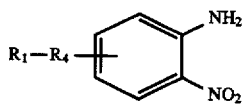

and coupling of the resulting diazonium salt onto a phenol of the formula

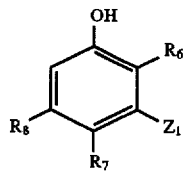

wherein, $R_1$ through $R_8$ are as previously defined; and $Z_1$=OW, or NHW where W is H, 1 to 20 carbon atom branched or unbranched alkyl, 2 to 10 carbon atom acyl, dialkyl carbamyl, or a substituted or unsubstituted aryl or heteroaryl sulfonyl group.

Compounds of formula (I) wherein $R_1$, $R_2$, $R_3$, $R_4$, $R_6$, $R_7$, are independently: H; halogen; $NH_2$; cyano; —$(CH_2)_p$ $CO_2Y$, where Y is H or a 1 to 12 (preferably 1 to 6) carbon atom alkyl, or 6 to 20 (preferably 6 to 10) carbon atom aryl group and p is 0–20; 1 to 12 (preferably 2 to 9) carbon atom carbamoyl group; 0 to 12 (preferably 2 to 4) carbon atom sulfoxido group; 0 to 12 (preferably 1 to 10) carbon atom sulfonyl group; 0 to 12 (preferably 1 to 10) carbon atom sulfonato group; 0 to 12 (preferably 1 to 10) carbon atom sulfonamido group; 1 to 18 (preferably 1 to 10) carbon atom alkyl group; 1 to 18 (preferably 1 to 10) carbon atom alkoxy group; 1 to 18 (preferably 1 to 10 carbon atom sulfido group; 6 to 20 (preferably 6 to 10) carbon atom aryl group; 5 to 20 (preferably 5 to 10) atom heteroaryl group having 1 to 4 (preferably 1 to 3) hetero atoms selected from O, N, S, P or Si; 6 to 20 (preferably 6 to 10) carbon atom aryloxy group; or any two or more of adjacent ones of $R_1$ through $R_4$ may form, together with the benzene ring to which they are attached, a 1 to 10 carbon atom alicyclic group, a 6 to 20 (preferably 6 to 10) carbon atom aromatic group or a 5 to 20 (preferably 5 to 10) atom heteroaryl group having 1 to 4 (preferably 1 to 3) heteroatoms selected from O, N, S, P or Si; R5 is H or an acetyl group, p-toluenesulfonyl group or dialkyl carbamyl group; $R_8$ is H or OX where X is H or a 1 to 6 carbon atom alkyl, acetyl, benzyl, benzoyl, p-toulenesulfonyl or dialkylcarbamyl group; Z is H, OH, a 1 to 6 carbon atom alkyl, 1 to 6 carbon atom alkoxy, 2 to 10 carbon atom acyloxy, 6 to 12 carbon atom arylsulfonyloxy, 6 to 12 atom dialkyl carbamato group or a group of the formula:

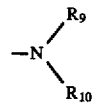

where each of $R_9$ and $R_{10}$ is independently H, or a 1 to 6 carbon atom alkyl group, 1 to 12 carbon atom acyl group, 6 to 20 carbon atom alkylsulfonyl, arylsulfonyl or heteroarylsulfonyl group, are preferably prepared by the process of this invention.

Of particular practical importance is the preparation of compounds of the formula (I) in which $R_2$ or $R_3$ or both are independently hydrogen or halogen atoms, preferably chlorine or fluorine atoms or O-alkyl or S-alkyl group.

When reference in this application is made to a substituent "group", this means that the substituent may itself be substituted or unsubstituted (for example "alkyl group" refers to a substituted or unsubstituted alkyl). Generally, unless otherwise specifically stated, substituents on any "groups" referenced herein or where something is stated to be possibly substituted, include the possibility of any groups, whether substituted or unsubstituted, which do not destroy properties necessary for the photographic utility. It will also be understood throughout this application that reference to a compound of a particular general formula includes those compounds of other more specific formula which specific formula falls within the general formula definition. Examples of substituents on any of the mentioned groups can include known substituents, such as: halogen, for example, chloro, fluoro, bromo, iodo; alkoxy, (for example, methoxy, ethoxy); substituted or unsubstituted alkyl, particularly lower alkyl (for example, methyl, trifluoromethyl); alkenyl or thioalkyl (for example, methylthio or ethylthio); substituted and unsubstituted aryl, (for example, phenyl); and substituted or unsubstituted heteroaryl (for example, pyridyl, thienyl, furyl, pyrrolyl); and others known in the art. With regard to any alkyl group, alkylene group or alkenyl group, it will be understood that these can be branched or unbranched and include ring structures.

The hydrogenation catalysts used according to the invention are PtS, Pt, Pd, Pt/Pd or Rh on a support. Suitable supports are those customarily used in the technology of hydrogenation catalysts, for example carbon (for example activated carbon, charcoal, peat charcoal), kieselguhr, alumina, barium sulfate and the like. Carbon is preferred as support. Preferred catalysts according to the invention are Pt, Pd, or Pt/Pd, in particular Pd/Pt, preferably in a ratio of Pt to Pd of 1:4, on a carbon support.

The amount of noble metal on the support (amount deposited) is in the range customary for hydrogenation catalysts. It is, for example, 0.1 to 10%, for example 0.5 to 10%, preferably 1 to 10%, in particular 3 to 10%. Amounts of 3 to 7%, for example about 4%, in each case relative to the weight of support material, are particularly advantageous.

The catalyst is advantageously used in an amount of 0.1–8%, in particular 0.5–5%, for example 1.0–3%, relative to the o-nitroazo compound used. It will be appreciated that the catalyst is recyclable, advantageously by filtration, if the process is carried out batchwise. The nature or physical properties of the noble metal catalysts remains essentially unchanged even after remaining in contact in the reaction mixture with organic or inorganic acids in accordance with this invention.

The base can be an organic amine, ammonia, preferably in the form of ammonium hydroxide, or an alkali metal hydroxide, such as sodium or potassium hydroxides or an alkaline earth metal hydroxide, such as calcium or magnesium hydroxides. Any organic amine known in the art can be used. Preferred amines having at least one —NH— or $NH_2$ group.

Primary, secondary or tertiary organic amines which can be used in the process according to the invention advantageously contain $C_0$ to $C_{18}$ atoms in the form of unbranched or branched alkyl groups. The most preferred amines are tertiary-butylamine, n-butylamine, methylamine, ethylamine, iso-propylamine, propylamine, ammonia and the like. Aromatic amines such as aniline can also be used, but generally useful only in unusual circumstances. It is of course also possible to use mixtures of two or more of the amines mentioned in the process according to the invention. Lower alkylamine may be easily recovered by simple distillation, if desired, for recycling. In certain cases aqueous or non-aqueous alkali hydroxides such sodium hydroxide or potassium hydroxide and the like or trialkylamine such as triethylamine can be used.

The organic amine is present in the reaction mixture advantageously in an amount of at least 0.01 mole, in particular at least 0.1 mole, preferably at least 3 mole, up to about 10 mole per mole of o-nitroazo dye compound starting material. Molar ratio of amine:azo compound are particularly advantageously in the range of about 0.5:1 to 10:1, in particular about 4:1.

Any acid known in the art, preferably having at least one or more ionizable hydrogen atom, is particularly suitable for the process of the invention. The acid element, such as sulfur or phosphorus or arsenic or antimony or bismuth or the like, in the inorganic acids advantageously should be of lower oxidation states. The $pKa_1$ should be in the preferred range of 1.0 to 2.5, most preferably in the range of 1.8 to 1.9; and $pKa_2$ should be in the preferred range of 6.0 to 10.0, most preferably in the range of 6.0 to 7.0. The properties of these acids inhibit dehalogenation of halo-substituted compounds of formula (II). It is of course possible to use mixtures of two or more such acids of similar pKa's in the process according to the invention.

If dehalogenation of a halo-substituted compound of formula (II) is desired, certain organic acids with preferred pKa range of 4.0 to 5.5, most preferably with pKa range of 4.2 to 4.85, such as acetic acid, propionic acid, n-butyric acid, benzoic acid and the like can be used. Mixtures of two or more such acids of similar pKa's can be used in this embodiment of the invention.

Absence of an acid not only gives quite low yields of benzotriazoles of formula(I) but also produces numerous undesired side products. The effectiveness and importance of ionizable protons of the acids of the present invention is demonstrated by using their sodium salt or potassium salt analogs instead of acid themselves while making no changes in other reactants. With alkali salts, 25–40% of N-oxide (as a result of incomplete reduction) and in some cases 5–10% over-reduced products are observed. Therefore, a free proton source (from the acids) and, in certain preferred embodiments, lower oxidation state of the acid elements seem to play the key role for clean conversion to benzotriazoles of formula(I).

The importance of the acid is also demonstrated by the fact that an anticipated hydrogen-transfer mechanism (i.e. H from acids being transferred to azo compounds of formula (II)) during the catalytic hydrogenation process is not operational at least to a significant extent is demonstrated by using a well-known hydrogen transferring reagent, such as 1,4-dihydroquinone, in place of acid(s) but in presence of all remaining reactants under reaction conditions of this invention. Under this condition not only dechlorination occurs but over-reduction of the benzo ring predominates by a factor of three. Therefore, an appropriate acid is essential for clean conversion to benzotriazoles of formula (I).

The acid(s) of the present invention is present in the reaction mixture advantageously in an amount of at least 0.01 mole, in particular at least 0.1 mole, preferably at least 3 mole, up to about 10 mole per mole of o-nitroazo dye compound starting material. Molar ratio of acid:azo compound are particularly advantageously in the range of about 0.5:1 to 10:1, in particular about 3:1.

The process according to the invention is carried out in a hydroxylic solvents, such as water, butanol, sec-butanol, isobutanol, isopropanol, n-propanol, ethanol, methanol or any combination of these. Occasionally if desired for solubility reasons, a non-hydroxylic solvent may also be used. Non-hydroxylic solvents that can be used include, for example, acyclic or cyclic ethers for example diglyme or tetrahydrofuran, or other non-hydroxylic solvents, such as, ethyl acetate, heptane, hexane, toluene, xylene, dimethyl acetamide, dimethylformamide, 1,3-dimethyl-3,4,5,6-tetrahydro-2(1H)pyrimidinone, 1,3-dimethyl-2-imidazolidinone, 1,1,3,3-tetramethyl urea, etc. may be used as co-solvents in the reaction mixture. A preferred reaction medium for the process of this invention comprises a hydroxylic solvent and a non hydroxylic solvent. A surfactant, such as sodium dodecylsulfonate, or a phase-transfer catalyst, such as tetraalkyl ammonium or tetraalkyl phosphonium halide, or the like can also be present. The acid-amine combination of the reaction medium may also serve as a phase-transfer catalyst. A particularly preferred reaction medium for the process of this invention is methanol or a methanol-water mixture.

The process according to the invention can be carried out batchwise but also continuously. For the continuous process, in particular a fixed bed catalyst, for example a high-pressure fixed bed hydrogenation unit, is suitable. In this case the reaction mixture is removed continuously and fed with fresh o-nitro azo dye compound+amine/ammonia/ hydroxide base+acid+solvent.

The hydrogenation is advantageously carried out at temperatures of 0°–120° C., for example, 15°–100° C., in particular 20°–80° C. Reaction temperatures of 30°–85° C., in particular 40°–70° C., for examples 50°–60° C., are particularly advantageous.

The hydrogenation pressure during the hydrogenation can be, for example, in the range of 0–130,000 $Kg/m^2$, for example, 0–70,000 $Kg/m^2$, in particular 3,000–60,000 $Kg/m^2$, and most preferably 50,000–60,000 $Kg/m^2$. Which hydrogen pressure is employed depends mainly on the hydrogenation unit available and the type of o-nitroazo dye compound. Higher pressure tends to cause more N—N bond cleavage if the N=N double bond character in the azo dye is decreased due to some specific substituents in both aromatic rings.

The hydrogenation time can vary within wide limits; it depends on the catalyst used, the hydrogen pressure, the reaction temperature and the unit used. It can be from a few minutes to several hours.

This invention details the following general procedure of catalytic hydrogenation of any of the o-nitroazo dye compound of formula(II) to benzotriazole derivatives of formula (I). To a 500 mL capacity stainless steel autoclave equipped with a stirrer, external heating jacket and internal heating and cooling coils is added 0.0115 mole of o-nitroazo dye compound of formula(II), 0.25 g (dry weight) of (4% Pd/C+1% Pt/C) catalyst (obtainable from Johnson Matthey or some other supplier), 4 mole equivalent (with respect to the azo dye compound) of tert-butylamine, 3 mole equivalent (with respect to the azo dye compound) of 50% aqueous hypophosphorous acid or sulfurous acid and 150 mL of methanol. The autoclave is purged with nitrogen gas and then hydrogen gas and then sealed and charged with hydrogen gas to a pressure of 53,000 Kg/m². The reaction is stirred at room temperature at a pressure of 53,000 Kg/m² (recharging if necessary) for one hour. After one hour the temperature is raised to 50° C. and held at the same temperature and pressure for an additional 12 hours while recharging the hydrogen as necessary. Then the autoclave and its contents are cooled to 45°–47° C. and removed and filtered through a Celite filter aid pad to remove the catalyst. The catalyst and the residue on the filter pad are further washed with some methanol for complete recovery of the product.

The isolation of the final products from the reaction medium is carried out by conventional methods known to one skilled in the art. It varies, depending on the type of solvent used. The organic solvents are removed completely on a rotary evaporator or by a large scale distillation setup whenever recovery of easily distillable organic amine is important for recycling. The left-over residue is diluted with appropriate volume of brine (aqueous sodium chloride solution) and acidified with hydrochloric acid until Congo Red indicator paper turns blue. The precipitate is collected by filtration, washed with cold water and recrystallized from a suitable solvent.

The process according to the invention opens up an industrially particularly favorable and economical route for the preparation of benzotriazole derivatives of formula(I) in high purity and superior yields.

The examples which follow illustrate the process according to the invention in more detail. Therein and also in the remaining description and patent claims, percentages are by weight, unless stated otherwise.

EXAMPLE 1

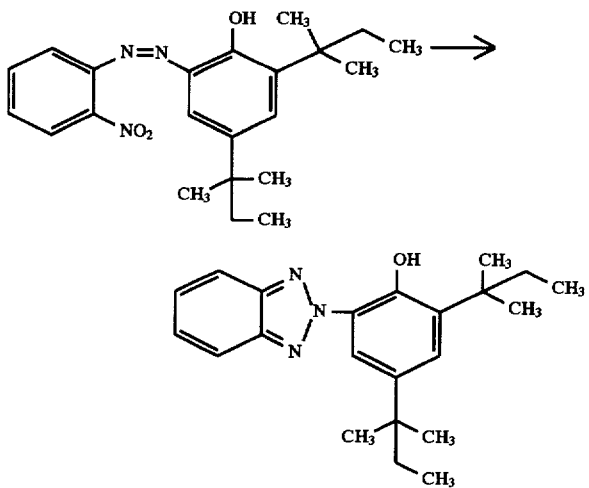

To a 500 mL capacity stainless steel autoclave equipped with a stirrer, external heating jacket and internal heating and cooling coils are added 5.0 g (0.013 mole) of 2-nitro-2'-hydroxy-3',5'-di-tert-amylazobenzene, 0.25 g (dry weight) of (4% Pd/C+1% Pt/C) catalyst, 3.82 g (0.052 mole, 4 equivalent) of tert-butylamine, 5.16 g (0.039 mole, 3 equivalent) of aqueous hypophosphorous acid and 150 mL of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter pad are further washed with some ethyl acetate for complete recovery of the product. The organic solvents are removed on a rotary evaporator. The residue is diluted with about 500 mL of brine (saturated aqueous sodium chloride solution) and treated with hydrochloric acid dropwise until the Congo Red Indicator paper turns blue. The light brown insoluble material (the desired product) was filtered on a sintered glass funnel, washed with cold distilled water to remove any contaminated salt, and air-dried. This crude solid material was recrystallized from isopropanol/water to obtain 4.56 g of 2-(2'-hydroxy-3',5'-di-tert-amylphenyl)benzotriazole as white solid (yield 99%; melting point 80°–81° C.) showing a retention time of 25.89 min. in HPLC analysis.

EXAMPLE 2

Example 1 is repeated, but with the difference that 3.58 g (about 4 molar equivalent) of 57.6% aqueous ammonium hydroxide instead of tert-butylamine, and 2.1 g (about 3 molar equivalent) of glacial acetic acid instead of hypophosphorous acid are used. No significant influence on the hydrogenation rate or yield is observable.

EXAMPLE 3

Examples 1 and 2 are repeated using either 5% Pd on activated carbon or 2–3% Pt on activated carbon as the catalyst. The product is then obtained in a yield of 90% of theory. About 8–10% (by peak area percent in HPLC analysis) of N-oxide intermediate is observed as a side product. This impurity is easily removable by silica gel flash column chromatography by eluting with heptane. Alternatively somewhat longer time in autoclave helps to eliminate this impurity by converting it to the desired product.

EXAMPLE 4

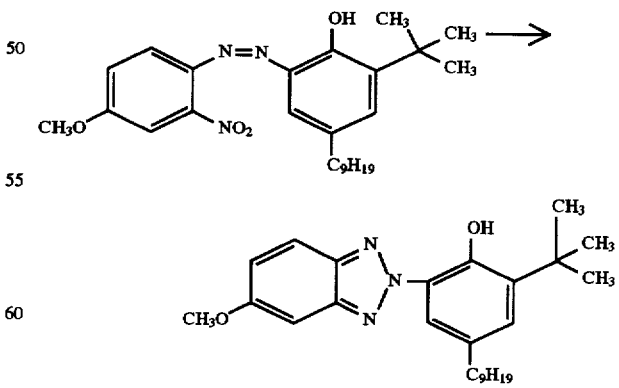

To a 500 mL capacity stainless steel autoclave equipped with a stirrer, external heating jacket and internal heating and cooling coils are added 5.0 g of (0.0082 mole) of 2-nitro-4-methoxy-2'-hydroxy-3'-t-butyl,5'-nonylazobenzene (nonyl group is an isomeric mixture) (purity 75%), 0.25 g (dry weight) of (4% Pd/C+1% Pt/C) catalyst, 3.2 g (about 4 equivalent) of tert-butylamine, 4.4 g (about 3 equivalent) of 50% aqueous hypophosphorous acid and 150 mL of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter pad are further washed with some tetrahydrofuran for complete recovery of the product. The organic solvents are removed on a rotary evaporator. The residue is diluted with about 500 mL of brine (saturated aqueous sodium chloride solution) and treated with hydrochloric acid dropwise until the Congo Red Indicator paper turns blue. The light purple insoluble liquid material (the desired product) is extracted with dichloromethane (200 mL), washed with brine (2×150 mL), dried (Na₂SO₄), filtered off and solvent is removed from the filtrate on a rotary evaporator to obtain 4.6 g of brown-purple colored viscous crude of 2-(2'-hydroxy-3'-t-butyl,5'-nonylphenyl)benzotriazole. After purifying by silica gel flash column eluting with heptane 2.93 g of nearly colorless liquid (yield 95%) is obtained. It shows a retention time of 27.3 min. in HPLC analysis and its FD-mass spectral analysis shows molecular ion peak at m/e 423.

EXAMPLE 5

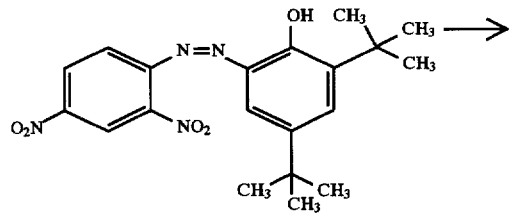

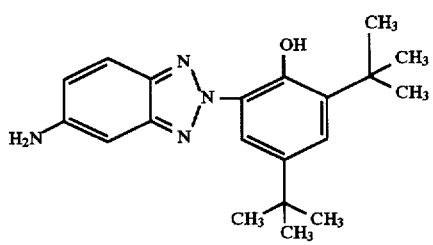

To a 500 mL capacity stainless steel autoclave equipped with a stirrer, external heating jacket and internal heating and cooling coils are added 4.53 g of (0.0091 mole) of 2,4-dinitro-2'-hydroxy-3', 5'-di-tert-butylazobenzene(purity 80%), 0.20 g (dry weight) of (4% Pd/C +1% Pt/C) catalyst, 3.3 g (about 4 equivalent) of tert-butylamine, 4.47 g (about 3 equivalenti of 50% aqueous hypophosphorous acid and 150 mL of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45° C.–47° C., removed and filtered through a Celite filter-aid pad to remove the catalyst. The catalyst and the residue on the filter pad are further washed with some ethyl acetate for complete recovery of the product. The organic solvents are removed on a rotary evaporator. The residue is diluted with about 500 mL of brine (saturated aqueous sodium chloride solution) and treated with hydrochloric acid dropwise until the Congo Red Indicator paper turns blue. The brown-light yellow crude solid was filtered on a sintered glass funnel, washed with cold water, and air-dried to obtain 3.09 g crude material of 2-(2'-hydroxy-3',5'-di-tert-butylphenyl)benzotriazole. After purifying by silica gel flash column eluting with ethyl acetate/heptane(1/1) 2.87 g light brown-yellow solid(yield 93%) is obtained. It shows a retention time of 22.3 min. in HPLC analysis and its FD-mass spectral analysis shows molecular ion peak at m/e 338.

This invention provides an excellent alternative to a traditional oxidative ring closure method employing the use of copper sulfate (an oxidizing agent of transition metal class, now an environmentally unacceptable chemical), as described by the following specific example given in the U.S. Pat. No. 3,761,272

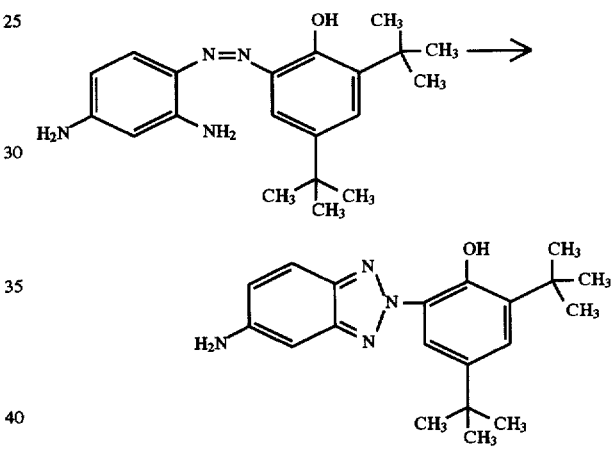

EXAMPLE 6

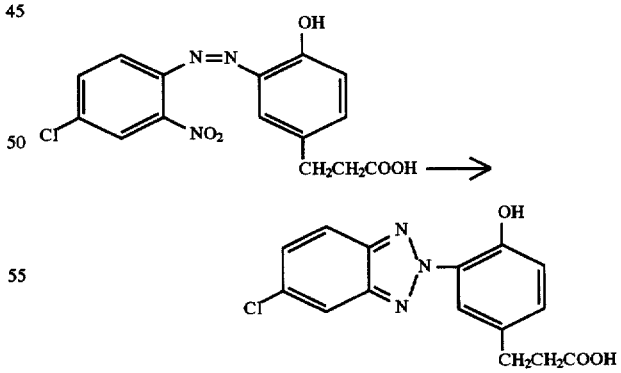

4-Chloro-2-nitro-2'-hydroxy-5'-(3-carboxyethyl) azobenzene (purity 65%) is made by a general procedure described in the Japanese Kokai Patent Application No. Sho 50[1975]-159484.

To a 4000 mL capacity stainless steel autoclave equipped with a stirrer, external heating jacket and internal heating and cooling coils are added 88.12 g (0.164 mole based on 65% purity) of 4-Chloro-2-nitro-2'-hydroxy-5'-(2-carboxyethyl)azobenzene of 65% purity, 4.4 g (dry weight) of (4% Pd/C+1% Pt/C) catalyst, 73.66 g (about 4 mole equivalent) of tert-butylamine, 99.75 g (about 3 mole equivalent) of 50% aqueous hypophosphorous acid and 3000 mL of methanol. The autoclave is purged with nitrogen gas and then hydrogen gas and then sealed and charged with hydrogen gas to a pressure of 53.000 Kg/m². The reaction is stirred at room temperature and at 53.000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter pad are further washed with some methanol for complete recovery of the product. The organic solvents are removed on a rotary evaporator. The residue is diluted with about 2000 mL of brine (saturated aqueous sodium chloride solution) and treated with hydrochloric acid dropwise until the Congo Red Indicator paper turns blue. The brown crude solid was filtered on a sintered glass funnel, washed with cold water, and air-dried to obtain 76.16 g crude solid material of 5-chloro-2H-[2'-hydroxy-5'-(2-carboxyethyl)phenyl]benzotriazole. After purifying by two recrystallizations from isopropanol/water mixture using decolorizing carbon, 47.94 g of white solid (yield 92%) is obtained. Its FD-mass spectral analysis shows molecular ion peak at m/e 317. It has a melting point of 169°–170° C. It UV absorption spectrum in methanol shows $\lambda_{max}$ at 341 nm with a molar extinction coefficient of 15,100.

EXAMPLE 7 (Comparative)

Example 6 is repeated under the reaction conditions given in the U.S. Pat. No. 5,187,289 (see Example 5 in Column 7 of this Patent). In addition to the desired product (about 40–50%), three other major compounds (structures given below) are obtained as a result of dehalogenation, side reaction and incomplete reduction, as identified by HPLC and FD-mass spectral analysis:

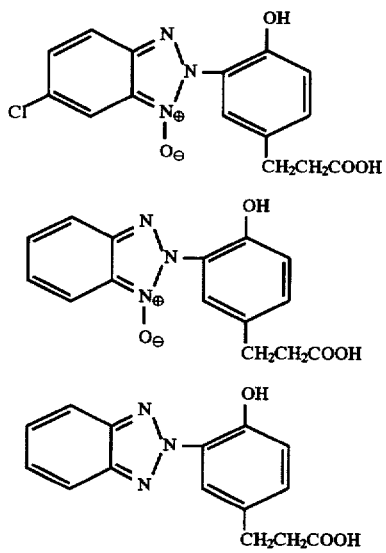

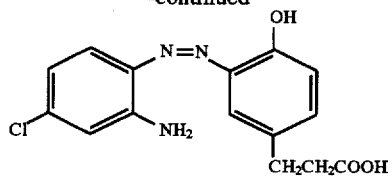

From this experiment it is clear that use of hypophosphorous acid, according to our invention, is essential to accomplish clean conversion to the desired product in an excellent yield. We do not observe any of these unwanted side products.

EXAMPLE 8 (Comparative)

Example 6 is repeated under the reaction conditions given in the U.S. Pat. No. 5,276,161 (see lines 11 through 21 in Column 5, Example 16 in Column 7 of this patent and also the claim No. 13 in Column 11), but without having hypophosphorous acid in the reaction mixture. In addition to the desired product (about 60–70%), three other major compounds (structures given below) are obtained as a result of incomplete reduction, over-reduction of the nitrophenyl ring and azo group, and N—N bond breakage as identified by HPLC and FD-mass spectral analysis. Because, in this experiment 5% Pt on carbon instead of 5% Pd on carbon is used as a catalyst, no dechlorination is observed at all as expected; however substantial amounts of following side products is observed:

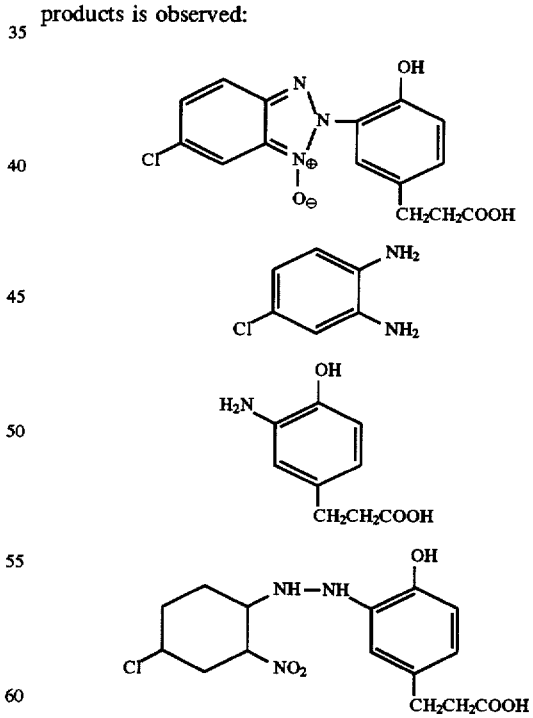

From this experiment it is clear that use of hypophosphorous acid, according to our invention, is essential to accomplish clean conversion to the desired product in an excellent yield. We do not observe any of these unwanted side products.

EXAMPLE 9

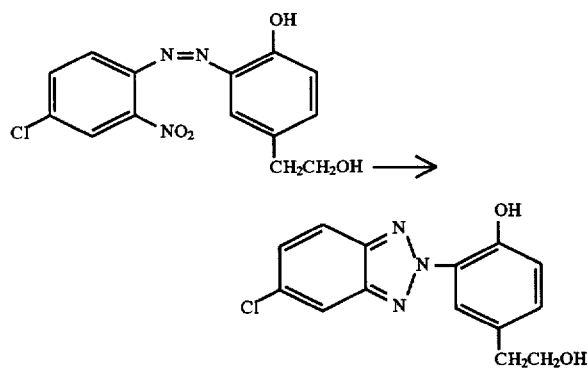

4-Chloro-2-nitro-2'-hydroxy-5'-(2-hydroxyethyl) azobenzene (purity 70%) is made by a general procedure described in the Japanese Kokai Patent Application No. Hei 3[1991]-236390.

To a 500 mL capacity stainless steel autoclave equipped with a stirrer, external heating jacket and internal heating and cooling coils are added 5.0 g (0.011 mole based on 70% purity) of 4-Chloro-2-nitro-2'-hydroxy-5'-(2-hydroxyethyl) azobenzene of 70% purity, 0.25 g (dry weight) of (4% Pd/C+1% Pt/C) catalyst, 4.54 g (about 4 mole equivalent) of tert-butylamine, 6.15 g (about 3 mole equivalent) of 50% aqueous hypophosphorous acid and 150 mL of methanol. The autoclave is purged with nitrogen gas and then hydrogen gas and then sealed and charged with hydrogen gas to a pressure of 53,000 Kg/m$^2$. The reaction is stirred at room temperature and at 53,000 Kg/m$^2$ pressure (recharging if necessary) for one hour. After one hour the temperature is raised to 50° C. and held at the same temperature and pressure for an additional 12 hours. Then the autoclave and its contents are cooled to 45° C.–47° C., removed and filtered through a Celite filter-aid pad to remove the catalyst. The catalyst and the residue on the filter pad are further washed with some methanol for complete recovery of the product. The organic solvents are removed on a rotary evaporator. The residue is diluted with about 200 mL of brine (saturated aqueous sodium chloride solution) and treated with hydrochloric acid dropwise until the Congo Red Indicator paper turns blue. The brown crude solid was filtered on a sintered glass funnel, washed with cold water, and air-dried to obtain 4.78 g crude solid material of 5-chloro-2H-[2'-hydroxy-5'-(2-hydroxyethyl)phenyl] benzotriazole. The crude material was purified by silica gel flash column chromatography eluting with a 9/1 mixture of dichloromethane and methanol. The product was obtained as a white solid, 3.12 g (98% yield), having melting point 128°–129° C., showing a retention time of 14.68 min. in HPLC, and molecular ion at m/e 289 in its FD-mass spectral analysis. It UV absorption spectrum in methanol shows $\lambda_{max}$ at 341 nm with a molar extinction coefficient of 15,200. Its $^1$H-NMR in DMSO-d$_6$ (with tetramethylsilane as an internal reference) shows peaks a δ 10.5 (broad peak, 1H, phenolic OH), 8.2 (s, 1H, arom.), 8.1 (d, 1H, arom.), 7.6 (s, 1H, arom.), 7.5 (d, 1H, arom.), 7.25 (d, 1H, arom.), 7.1 (d, 1H, arom.), 3.6 (t, 2H, CH$_2$ attached to oxygen atom), 2.7 (t, 2H, CH$_2$ attached to the phenyl ring), 1.2 (s, 1H, primary alcoholic proton).

Similarly, 5-chloro-2H-[2'-hydroxy-5'-(3-hydroxypropyl) phenyl]benzotriazole may be prepared from 4-Chloro-2-nitro-2'-hydroxy-5'-(3-hydroxypropyl)azobenzene.

EXAMPLE 10

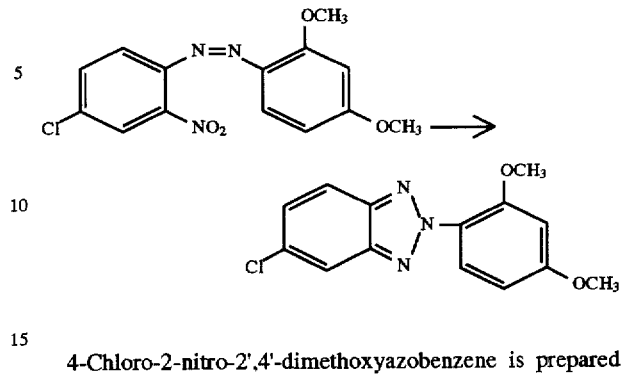

4-Chloro-2-nitro-2',4'-dimethoxyazobenzene is prepared by the procedure described in our U.S. Provisional Patent Application Serial No. 60/000,663 (Filed on Jun. 29, 1995).

To a 500 mL capacity stainless steel autoclave equipped with a stirrer, external heating jacket and internal heating and cooling coils are added 3.06 g (0.0095 mole) of 4-Chloro-2-nitro-2',4'-dimethoxyazobenzene, 0.153 g (dry weight) of (4% Pd/C+1% Pt/C) catalyst, 2.78 g (about 4 mole equivalent) of tert-butylamine, 3.77 g (about 3 mole equivalent) of 50% aqueous hypophosphorous acid and 150 mL of methanol. The autoclave is purged with nitrogen gas and then hydrogen gas and then sealed and charged with hydrogen gas to a pressure of 53,000 Kg/m$^2$. The reaction is stirred at room temperature and at 53,000 Kg/m$^2$ pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter pad are further washed with some methanol for complete recovery of the product. The organic solvents are removed on a rotary evaporator. The residue is diluted with about 200 mL of brine (saturated aqueous sodium chloride solution) and treated with hydrochloric acid dropwise until the Congo Red Indicator paper turns blue. The brown crude solid was filtered on a sintered glass funnel, washed with cold water, and air-dried to obtain 2.78 g crude solid material of 5-chloro-2H-(2',4'-dimethoxy phenyl)benzotriazole. The crude material was purified by silica gel flash column chromatography eluting with a 1/1 mixture of ethylacetate and heptane. The product was obtained as a off-white solid, 2.64 g (96% yield), showing a retention time of 16.2 min. in HPLC, and molecular ion at m/e 289 in its FD-mass spectral analysis. Its $^1$H-NMR in CDCl$_3$ (with tetramethylsilane as an internal reference) shows peaks at δ7.9 (m, 2H, arom.), 7.55 (d, 1H, arom.), 7.38 (d, 1H, arom.), 6.62 (m, 2H, arom.), 3.9 (s, 3H, methoxy), and 3.85 (s, 3H, methoxy). If desired, both methoxy groups can be cleanly converted to phenolic groups by the procedure described in our U.S. Provisional Patent Application Serial No. 60/000.663 (Filed on Jun. 29, 1995).

EXAMPLE 11

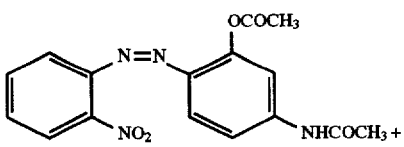

15
-continued

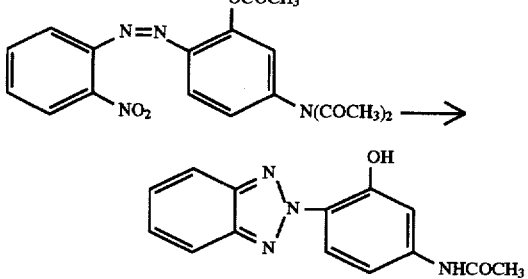

About 1:1 mixture 2-nitro-2'-acetoxy-4'-aminoacetyl/and 4'-aminodiacetylazobenzenes is prepared by the procedure described in our U.S. Provisional Patent Application Serial No. 60/000,663 (Filed on Jun. 29, 1995).

To a 500 mL capacity stainless steel autoclave equipped with a stirrer, external heating jacket and internal heating and cooling coils are added 7.15 g (about 0.02 mole) of about 1:1 mixture 2-nitro -2'-acetoxy-4'-aminoacetyl/and 4'-aminodiacetylazobenzenes, 0.358 g (dry weight) of (4% Pd/C+1% Pt/C) catalyst, 6.1 g (about 4 mole equivalent) of tert-butylamine, 8.28 g (about 3 mole equivalent) of 50% aqueous hypophosphorous acid and 215 mL of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter-pad are further washed with some methanol for complete recovery of the product. The organic solvents are removed on a rotary evaporator. The residue is diluted with about 200 mL of brine (saturated aqueous sodium chloride solution) and treated with hydrochloric acid dropwise until the Congo Red Indicator paper turns blue. The brown crude solid was filtered on a sintered glass funnel, washed with cold water, and air-dried to obtain 4.9 g crude light-brown solid material of 2H-(2'-hydroxy, 4'-aminoacetylphenyl)benzo triazole. The crude material was purified by silica gel flash column chromatography eluting with a 1/1 mixture of ethylacetate and heptane. The product was obtained as a off-white solid, 4.6 g (86% yield), showing a retention time of 13.27 min. in HPLC, and molecular ion at m/e 268 in its FD-mass spectral analysis. Its ¹H-NMR in CDCl₃ and two drops of DMSO-d₆ (with tetramethylsilane as an internal reference) shows peaks at δ11.7 (s, 1H, phenolic OH), 10.5 (s, 1H, CONH), 8.3 (d, 1H, arom.), 8.02 (m, 2H, arom), 7.82 (s, 1H, arom.), 7.6 (m, 2H, arom.), 7.38 (d, 1H, arom.), and 2.22 (s, 3H, COCH3). If desired, the aminoacetyl group can be cleanly converted to NH₂ group by the procedure described in our U.S. Provisional Patent Application Serial No. 60/000,663 (Filed on Jun. 29, 1995).

This Example illustrates the versatility of the process of this invention for the preparation of amino-substituted benzotriazoles of formula(I).

16
EXAMPLE 12

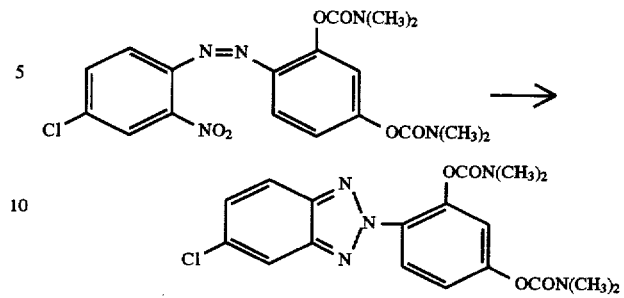

4-Chloro-2-nitro-2',4'-di-N,N-dimethylcarbamyloxy azobenzene or any of the 2',4'-dihydroxy/ and 2'-hydroxy, 4'-amino or substituted aminoazobenzene analogs are easily made with suitable protecting groups in excellent yield and often in 99% or greater purity) by following a general procedure described in our U.S. Provisional Patent Application Serial No. 60/000,663 (Filed on Jun. 29, 1995). The yields of such benzotriazole derivatives of general formula (I) obtained by the process of this invention vary from medium to excellent depending on the nature of the protecting groups present in the o-nitroazo dye compounds of general formula(II). The procedures for deprotection of such groups in compounds of formula(I) have been described in detail in the same U.S. patent application Ser. No. The following examples, which are traditionally carried out by now environmentally unacceptable zinc dust/aqueous alkali method in 50–55% yield, will further illustrate the versatility of this invention demonstrating clean conversion of azo dye compounds to the corresponding benzotriazoles in excellent yields.

To a 20 liter capacity stainless steel autoclave equipped with a stirrer, external heating jacket and internal heating and cooling coils are added 500 g (1.1472 moles) of 4-Chloro-2-nitro-2',4'-di-N,N-dimethyl carbamyloxyazobenzene, 25 g (dry weight) of (4% Pd/C+ 1% Pt/C) catalyst, 335 g (about 4 mole equivalent) of tert-butylamine, 454 g (about 3 mole equivalent) of 50% aqueous hypophosphorous acid and 12 liters of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter-pad are further washed with some methanol and ethyl acetate for complete recovery of the product. The organic solvents are removed on a rotary evaporator. The residue is diluted with 4 liters of brine (saturated aqueous sodium chloride solution) and treated with hydrochloric acid dropwise until the Congo Red Indicator paper turns blue. The light-brown crude solid was filtered on a sintered glass funnel, washed with cold water, and air-dried to obtain 461 g crude solid material of 5-chloro-2H-(2',4'-di-N,N-dimethylcarbamyloxyphenyl) benzotriazole. The crude material was purified by recrystalization from aqueous isopropanol. The product was obtained as a off-white solid, 420 g (91% yield), having melting point 138°–139° C., showing a retention time of 15.97 min. in HPLC in 100% purity by peak area, and molecular ion at m/e 403 in its FD-mass spectral analysis. It gives a characteristic blue fluorescence under the short wavelength UV light. Its ¹H-NMR in DMSO-d₆ (with tetramethylsilane as an internal reference) shows peaks at δ8.2 (s, 1H, arom.), 8.1 (t, 2H, arom.), 7.55 (d, 1H, arom.), 7.3 (d, 2H, arom.), 3.1 (s, 3H, N—CH3), 2.95 (two singlets, 6H, 2×N—CH₃'s), and 2.75 (s, 3H, N—CH₃).

EXAMPLE 13

When Example 12 is repeated on a smaller scale such as on a 5 g scale of 4-chloro-2-nitro-2',4'-di-N,N-dimethylcarbamyloxyazobenzene, similar result is obtained.

EXAMPLE 14

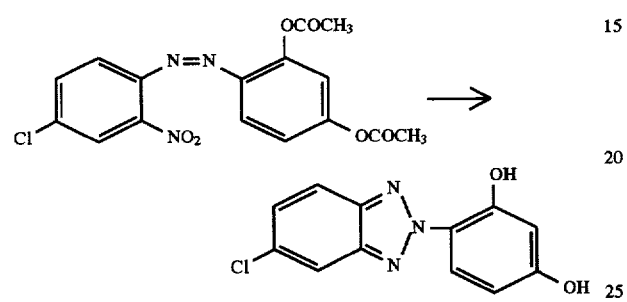

To a 500 mL capacity stainless steel autoclave equipped with a stirrer, external heating jacket and internal heating and cooling coils are added 5.0 g (0.0132 mole) of 2-nitro-4-chloro-2',4'-diacetoxyazobenzene, 0.25 g (dry weight) of (4% Pd/C+1% Pt/C) catalyst, 3.87 g (0.052 mole, 4 equivalent) of tert-butylamine, 5.2 g (0.039 mole, 3 equivalent) of 50% aqueous hypophosphorous acid and 150 mL of methanol. The autoclave is purged with nitrogen gas and then hydrogen gas and then sealed and charged with hydrogen gas to a pressure of 53,000 Kg/m². The reaction is stirred at room temperature and at 53,000 Kg/m² pressure (recharging if necessary) for one hour. After one hour the temperature is raised to 50° C. and held at the same temperature and pressure for an additional 12 hours. Then the autoclave and its contents are cooled to 45°–47° C., removed and filtered through a Celite filter-aid pad to remove the catalyst. The catalyst and the residue on the filter-pad are further washed with some methanol for complete recovery of the product. The organic solvents are removed on a rotary evaporator. The residue is diluted with about 500 mL of brine (saturated aqueous sodium chloride solution) and treated with hydrochloric acid dropwise until the Congo Red Indicator paper turns blue. The light brown insoluble material (the desired product) was filtered on a sintered glass funnel, washed with cold distilled water to remove any contaminated salt, and air-dried. This crude light-brown solid material was recrystallized from isopropanol/water mixture to obtain 2.3 g of 2H-(2',4'-dihydroxyphenyl)-5-chlorobenzotriazole as off-white solid (yield 63% of theory). This is characterized by its retention time of 15.03 min. in HPLC analysis and its molecular ion at m/e 261 in FD-mass spectral analysis.

This Example illustrates the usefulness of this invention where in situ deprotection of protecting groups such acyl or dialkylcarbamyl or alkylsulfonyl or arylsulfonyl or heteroarylsulfonyl is highly desirable.

EXAMPLE 15

Example 12 is repeated substituting the catalyst with 5% Pd on carbon while keeping hypophosphorous acid in the reaction mixture. This experiment is done to demonstrate the retention of the 5-chloro substituent in 5-chloro-2H-(2',4'-di-N,N-dimethylcarbamyloxyphenyl)benzotriazole product. Surprisingly dechlorination occurs <3% even after keeping the reaction mixture at 50° C. for considerably long hours such as for 12 hours.

From this experiment of our invention it is clear that halogen substituents are, indeed, retained in the product regardless of the type of noble metal hydrogenation catalyst.

EXAMPLE 16

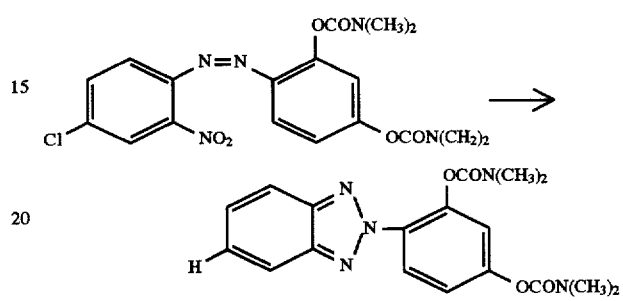

Example 12 is repeated substituting the hypophosphorous acid with glacial acetic acid to illustrate the influence of change in pKa of the acid(s) of this invention. The completely dechlorinated product 2H-(2',4'-di-N,N-dimethylcarbamyloxyphenyl)benzotriazole was obtained in 87% yield as characterized by its retention time, 14.06 min., in HPLC analysis and its molecular ion at m/e 369 in FD-mass spectral analysis.

This example illustrates the usefulness of this invention where dehalogenation in such a process is highly desirable.

EXAMPLE 17

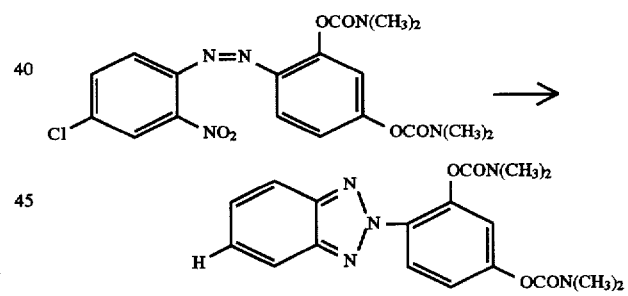

Example 12 is repeated substituting the hypophosphorous acid with propionic acid to illustrate the influence of change in pKa of the acid(s) of this invention and to further illustrate that acids of similar characteristics afford the similar results. Such as in this Example, glacial acetic acid in Example 13 has been replaced by propionic acid. Again, the completely dechlorinated product 2H-(2',4'-di-N,N-dimethylcarbamyloxyphenyl)benzotriazole is obtained in similar yield as characterized by its retention time, 14.06 min., in HPLC analysis and its molecular ion at m/e 369 in FD-mass spectral analysis.

This example again illustrates the usefulness of this invention where dehalogenation in such a process is highly desirable. This further illustrates that only suitable pKa of the acids and appropriate, preferably, lower oxidation state of the acid-element, such as sulfur, phosphorus and the like, are essential for clean conversion of o-nitroazo dye compounds of formula(II) to benzotriazole derivatives of formula(I) with complete retention of halogen substituents, particularly when Pd on carbon is used as a hydrogenation catalyst.

The invention has been described in detail with particular reference to preferred embodiments, but it will be understood that variations and modifications can be effected within the spirit and scope of the invention.

What is claimed is:

1. A process for the preparation of 2-(2'-hydroxyphenyl)-2H-benzotriazole derivatives of the formula (I):

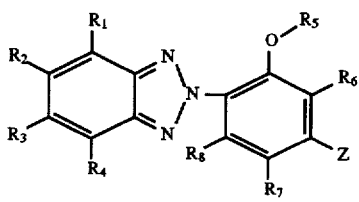

wherein $R_1$, $R_2$, $R_3$, $R_4$, $R_6$, $R_7$, are independently: H; halogen; $NH_2$; cyano; —$(CH_2)_pCO_2Y$ where Y is H or a 1 to 12 carbon atom alkyl or 6 to 20 carbon atom aryl and p is 0 to 20; 1 to 12 carbon atom carbamoyl group; 0 to 12 carbon atom sulfido group; 0 to 12 carbon atom sulfonyl group; 0 to 12 carbon atom sulfonato group; 0 to 12 carbon atom sulfonamido group; 1 to 18 carbon atom alkyl group; 1 to 18 carbon atom alkoxy group; 1 to 18 carbon atom sulfido group; 6 to 20 carbon atom aryl group; 5 to 20 atom heteroaryl group having 1 to 4 hetero atoms selected from O, N, S, P or Si; 6 to 20 carbon atom aryloxy group; or any two or more of adjacent ones of $R_1$ through $R_4$ may form, together with the carbon atoms of the benzene ring to which they are attached, a 1 to 10 carbon atom alicyclic group, a 6 to 20 carbon atom aromatic group or a 5 to 20 atom heteroaryl group having 1 to 4 heteroatoms selected from O, N, S, P or Si;

$R_5$ is H, acetyl, p-toluenesulfonyl or dialkylcarbamyl;

$R_8$ is H or OX where X is H or a 1 to 6 carbon alkyl, acetyl, benzyl, benzoyl, p-toulenesulfonyl or dialkylcarbamyl group;

Z is H, OH, a 1 to 6 carbon atom alkyl, 1 to 6 carbon atom alkoxy, 2 to 10 carbon atom acyloxy, to 12 carbon atom arylsulfonyloxy or 2 to 12 carbon atom dialkylcarbamato group or a group of the formula:

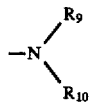

wherein each of $R_9$ and $R_{10}$ is independently H, 1 to 6 carbon atom alkyl group, 1 to 12 carbon atom acyl group, 6 to 20 carbon atom alkylsulfonyl group, arylsulfonyl group, heteroarylsulfonyl group, or a 2 to 12 carbon atom dialkylcarbamato group, said process comprising the catalytic hydrogenation of an azo dye compound of formula (II)

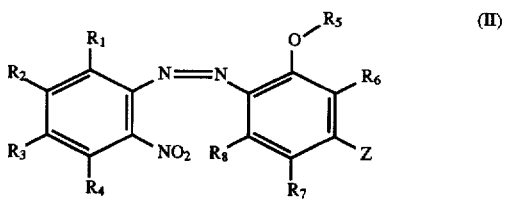

wherein $R_5$–$R_8$ and Z are as defined above for formula I, and $R_1$–$R_4$ are as defined above or a $NO_2$ group, in the presence a noble metal hydrogenation catalyst, a base and an acid in a reaction medium comprising a polar hydroxylic solvent and, optionally, a non-hydroxylic solvent.

2. A process according to claim 1, wherein the catalyst is selected from PtS, and Pt, Pd, Pt/Pd or Rh on a support.

3. A process according to claim 2, wherein the catalyst is Pt/Pd on a support.

4. A process according to claim 3, wherein the ratio of Pt to Pd is about 1:4.

5. A process according to claim 4, wherein the amount of base is used is at least four molar equivalent to the o-nitroazo dye compound of formula(II).

6. A process according to claim 4, wherein the amount of base used is at least three molar equivalent to the o-nitroazo dye compound of formula(II).

7. A process according to claim 4, wherein the molar equivalence base and of acid, to that of o-nitroazo dye compounds of formula(II) is in a ratio of about 4:3.

8. A process according to claim 1, wherein the base is an organic amine selected from cyclic and acyclic amines.

9. A process according to claim 8, wherein the amine is a primary or a secondary amine.

10. A process according to claim 9, wherein the amine is tert-butylamine.

11. A process according to claim 1, wherein the base is ammonia in the form of ammonium hydroxide.

12. A process according to claim 1, wherein the base is an alkali metal hydroxide or an alkaline earth metal hydroxide.

13. A process according to claim 1, wherein the acid is hypophosphorous acid, phosphorus acid, sulfurous acid, sulfinic acid or a 2 to 10 carbon atom aliphatic acid.

14. A process according to claim 13, wherein the acid is hypophosphorous acid or sulfurous acid.

15. A process according to claim 1, wherein the compound of formula I contains one or more halogen atoms and the hydrogenation is carried out in the presence of a 2 to 10 carbon atom aliphatic acid so as to remove the halogen atoms.

16. A process according to claim 1, wherein the amount of acid used is at least 0.01 mole per mole of the nitroazo dye compound of formula (II).

17. A process according to claim 1, wherein the amount of acid used is at least 3 mole per mole of the nitroazo dye compound of formula (II).

18. A process according to claim 1, wherein the hydroxylic solvent is water or a 1 to 10 carbon atom alcohol.

19. A process according to claim 1, wherein the reaction medium comprises a 1 to 10 carbon atom aliphatic alcohol and water.

20. A process according to claim 1, wherein the reaction medium comprises a hydroxylic solvent, a non-hydroxylic solvent and a surfactant or a phase-transfer catalyst.

21. A process according to claim 18, wherein the non-hydroxylic solvent is tetrahydrofuran, noncyclic ethers, ethyl acetate, heptane cyclohexane, toluene, xylene, dimethylformamide, dimethyl acetamide, 1,3-dimethyl-3,4,5,6-tetrahydro-2(1H)pyrimidinone, 1,3-dimethyl-2-imidazolidinone, 1,1,3,3-tetramethyl urea.

22. A process according to claim 1, wherein the hydrogenation reaction is conducted at a temperature of about 20° to about 100° C.

23. A process according to claim 1, wherein the hydrogenation reaction is conducted at a pressure of about 3,000 to about 50,000 Kg/m²).

24. A process according to claim 1, wherein the catalyst is Pt/Pd on carbon in a ratio of platinum to palladium is about 1:4, the base is used in amount of about 4 molar equivalent to the compound of formula II, the acid is used in an amount of about 3 molar equivalent to the compound of formula II, the hydroxylic solvent is methanol and the reaction is carried out under pressure of about 70 to 80 psig (about 50,000 to 60,000 Kg/m²) and the temperature of about 40° to 60° C.

* * * * *